United States Patent
Ho et al.

(10) Patent No.: US 11,547,730 B2
(45) Date of Patent: Jan. 10, 2023

(54) THERAPY FOR POLYGLUTAMINE (POLYQ) DISEASES

(71) Applicant: STEMINENT BIOTHERAPEUTICS INC., Taipei (TW)

(72) Inventors: Jennifer Hui-Chun Ho, San Diego, CA (US); Ryan Chang, Taipei (TW); Hsiu-Yu Lai, Taipei (TW); Wei-Kee Ong, Taipei (TW)

(73) Assignee: STEMINENT BIOTHERAPEUTICS INC., Taipei (TW)

( * ) Notice: Subject to any disclaimer, the term of this patent is extended or adjusted under 35 U.S.C. 154(b) by 202 days.

(21) Appl. No.: 16/617,241

(22) PCT Filed: May 26, 2017

(86) PCT No.: PCT/US2017/034831
§ 371 (c)(1),
(2) Date: Nov. 26, 2019

(87) PCT Pub. No.: WO2018/217216
PCT Pub. Date: Nov. 29, 2018

(65) Prior Publication Data
US 2021/0260127 A1    Aug. 26, 2021

(51) Int. Cl.
  A61K 35/28      (2015.01)
  A61P 25/28      (2006.01)
  A61K 9/00       (2006.01)
  A61K 35/35      (2015.01)

(52) U.S. Cl.
  CPC .......... *A61K 35/28* (2013.01); *A61K 9/0019* (2013.01); *A61K 35/35* (2013.01); *A61P 25/28* (2018.01)

(58) Field of Classification Search
  None
  See application file for complete search history.

(56) References Cited

U.S. PATENT DOCUMENTS

2012/0288480 A1   11/2012  Ho
2013/0023046 A1   1/2013   Ginard
2015/0216908 A1   8/2015   Lee et al.

FOREIGN PATENT DOCUMENTS

TW           201538728 A      10/2015

OTHER PUBLICATIONS

Benraiss A, Goldman SA. Cellular therapy and induced neuronal replacement for Huntington's disease. Neurotherapeutics. Oct. 2011;8(4):577-90. (Year: 2011).*
Siska EK, Koliakos G, Petrakis S. Stem cell models of polyglutamine diseases and their use in cell-based therapies. Front Neurosci. Jul. 14, 2015;9:247. (Year: 2015).*
Kean TJ, Lin P, Caplan AI, Dennis JE. MSCs: Delivery Routes and Engraftment, Cell-Targeting Strategies, and Immune Modulation. Stem Cells Int. 2013;2013:732742. (Year: 2013).*
Ankrum JA, Ong JF, Karp JM. Mesenchymal stem cells: immune evasive, not immune privileged. Nat Biotechnol. Mar. 2014;32(3):252-60. (Year: 2014).*
Golpanian S, Schulman IH, Ebert RF, et al. Concise Review: Review and Perspective of Cell Dosage and Routes of Administration From Preclinical and Clinical Studies of Stem Cell Therapy for Heart Disease. Stem Cells Transl Med. 2016;5(2):186-191. (Year: 2016).*
Srijaya TC, Ramasamy TS, Kasim NH. Advancing stem cell therapy from bench to bedside: lessons from drug therapies. J Transl Med. 2014;12:243. (Year: 2014).*
Lee ST, Chu K, Jung KH, Im WS, Park JE, Lim HC, Won CH, Shin SH, Lee SK, Kim M, Roh JK. Slowed progression in models of Huntington disease by adipose stem cell transplantation. Ann Neurol. Nov. 2009;66(5):671-81. (Year: 2009).*
Kim BR, Lim JH, Lee SA, et al. Usefulness of the Scale for the Assessment and Rating of Ataxia (SARA) in Ataxic Stroke Patients. Ann Rehabil Med. 2011;35(6):772-780 (Year: 2011).*
Zhang J, Huang X, Wang H, et al. The challenges and promises of allogeneic mesenchymal stem cells for use as a cell-based therapy. Stem Cell Res Ther. 2015;6:234. (Year: 2015).*
Extended European Search Report in European counterpart Application No. 17911016.8, dated Dec. 21, 2020, in 17 pages.
Jin, Jia-Li, et al. "Safety and efficacy of umbilical cord mesenchymal stem cell therapy in hereditary spinocerebellar ataxia." Current Neurovascular Research 10.1 (2013): 11-20.
Tsai, Yun-An, et al. "Treatment of spinocerebellar ataxia with mesenchymal stem cells: a phase I/IIa clinical study" Cell Transplantation 26.3 (2017): 503-512.
Suto, Nana, et al. "Morphological and functional attenuation of degeneration of peripheral neurons by mesenchymal stem cell-conditioned medium in spinocerebellar ataxia type 1-knock-in mice." CNS Neuroscience & Therapeutics 22.8 (2016): 670-676.
Office Action in Taiwan Counterpart Application No. 106117754, dated Jun. 18, 2020, in pages; English translation provided.
Chang, You-Kang, et al. "Mesenchymal stem cell transplantation ameliorates motor function deterioration of spinocerebellar ataxia by rescuing cerebellar Purkinje cells." Journal of Biomedical Science 18.1 (2011):54, 9 pages.
Zhang, Mei-Juan, et al. "Human umbilical mesenchymal stem cells enhance the expression of neurotrophic factors and protect ataxic mice" Brain Research 1402 (2011): 122-131.

* cited by examiner

*Primary Examiner* — Marcia S Noble
(74) *Attorney, Agent, or Firm* — Pilloff Passino & Cosenza LLP; Sean A. Passino; Rachel K. Pilloff

(57) ABSTRACT

Provided are methods and articles of manufacture for use in stem cell therapy, for the treatment of diseases or conditions of SCA. Particularly, the invention provides a method for treating SCA, comprising parenterally or locally administering an effective amount of stem cells as a unit dosage to a subject, wherein the administration is performed with one or more treatment cycles, wherein one treatment cycle comprises dosing three unit dosages each at a dosing interval of two to six weeks.

13 Claims, 15 Drawing Sheets
(8 of 15 Drawing Sheet(s) Filed in Color)

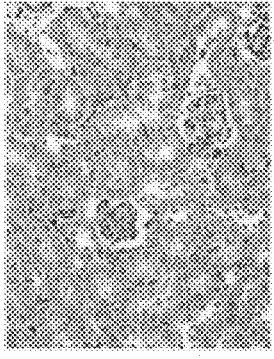
FIG. 2A
FIG. 2B
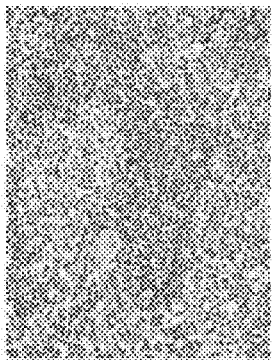
FIG. 2C
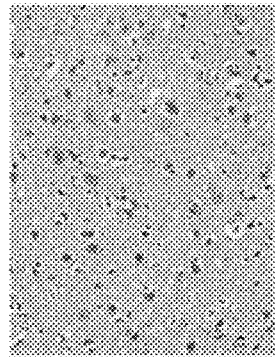
FIG. 2D
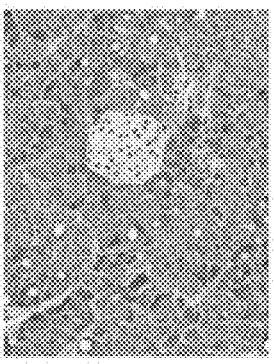
FIG. 2E
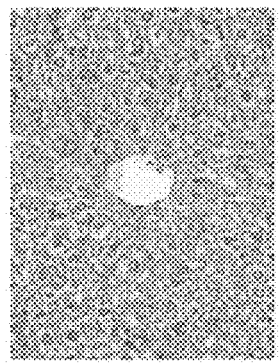
FIG. 2F
FIG. 2G FIG. 8
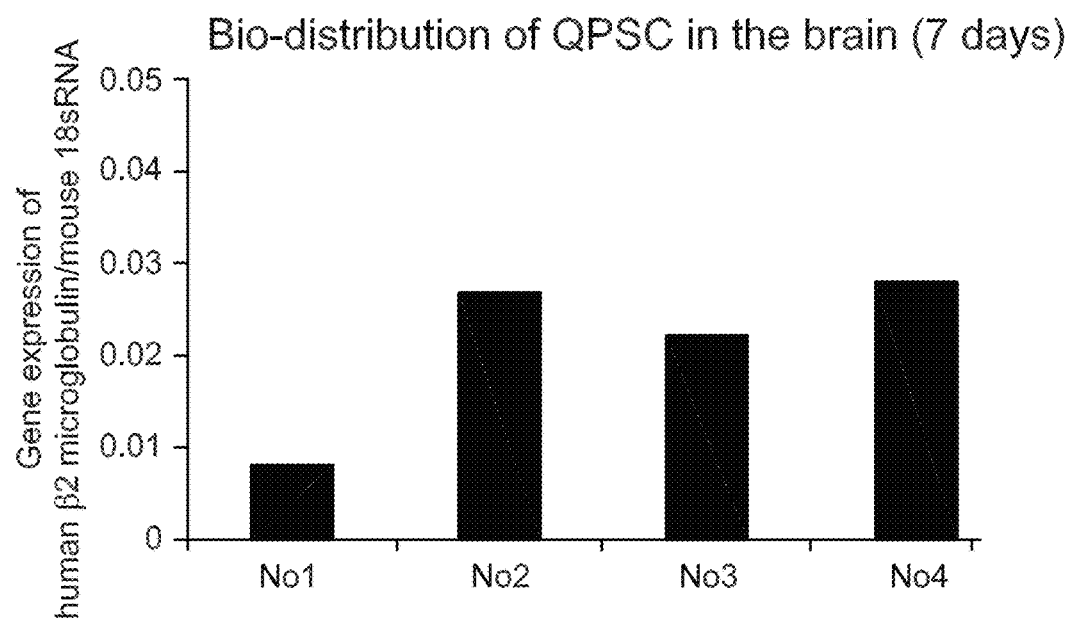
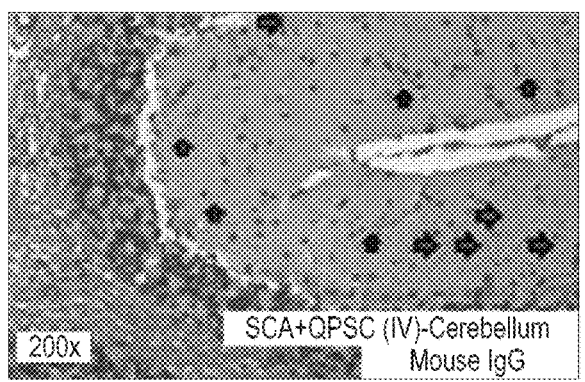
FIG. 9A
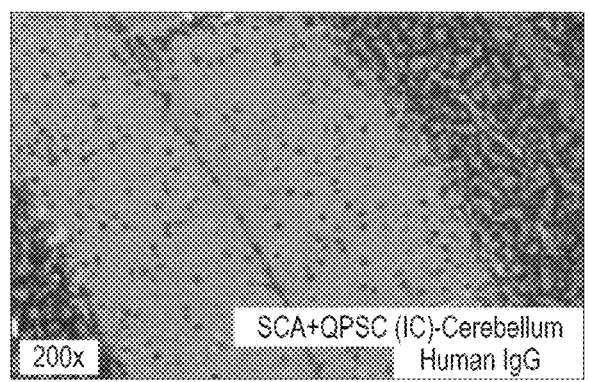
FIG. 9B

THERAPY FOR POLYGLUTAMINE (POLYQ) DISEASES This application is a U.S. National Phase 371 Application of International Application No. PCT/US2017/034831, filed May 26, 2017, the content of which is incorporated by reference herein in their entirety.

FIELD OF THE INVENTION

The invention relates to the field of a therapy for neurodegenerative disorder. Particularly, the invention pertains to a therapeutic regimen for treating a polyglutamine (polyQ) disease with stem cells.

BACKGROUND OF THE INVENTION

Ataxias are a clinically and genetically heterogeneous group of neurodegenerative diseases that variably affect the cerebellum, brainstem, and spinocerebellar tracts. Spinocerebellar ataxia (SCA) is progressive, degenerative, and fatal. SCA includes degeneration of neuronal tissues in which the main locus of pathological change exists in the nucleus or neural pathway of cerebellum, brain stem or spinal cord. The fetal conditions of SCA come from not only extensive neuron loss, but also bedridden and respiratory failure at the end-staged disease. The most common of SCA generic subtypes are poly-glutamine (polyQ) mediated SCA, i.e., SCA1, SCA2, SCA3, SCA6, SCA7 and SCA17.

U.S. Pat. No. 7,067,545 provides a method for treating spincerebellar degeneration which comprises administering to a patient with this disease an efficacious dose of one or more members selected from among D-cycloserine, D-serine esters, D-serine and salts thereof. U.S. Pat. No. 9,125,924 relates to a method of alleviating a sign or symptom of SCA by intravenously administering an aqueous formulation comprising trehalose.

However, there is no effective medical treatment or potential cure for SCA. Accordingly, there is a need for therapeutic methods for alleviating the signs and symptoms of SCA.

SUMMARY OF THE INVENTION

The invention provides a method for treating a polyglutamine (polyQ) disease in a subject, comprising parenterally or locally administering an effective amount of stem cells as a unit dosage to a subject, wherein the administration is performed with one or more treatment cycles, wherein one treatment cycle comprises dosing three unit dosages each at a dosing interval of two to six weeks.

In some embodiment, the polyQ diseases include, but are not limited to, spinocerebellar ataxias (SCA); Machado-Joseph disease (MJD/SCA3); Huntington's disease (HD); dentatorubral pallidoluysian atrophy (DRPLA); and spinal and bulbar muscular atrophy, X-linked 1 (SMAX1/SBMA). In one embodiment, the SCA is SCA1, SCA2, SCA3, SCA6, SCA7 or SCA17.

In some embodiments, the mesenchymal stem cells are mesenchymal stem cell population (MSC), adipose tissue-derived stem cell (ADMSC) population, orbital fat-derived stem cell (OFSC) population or quadri-positive stromal cell (QPSC) population.

In some embodiments, the cells can be administered by parenteral administration or local treatment (such as intra-brain or intracranial administration).

In some embodiments, the unit dosage ranges from $0.5 \times 10^5$ to $5 \times 10^{10}$ cells/kg body weight.

In one embodiment, the administration is performed with one or more treatment cycles, wherein one treatment cycle comprises dosing three unit dosages each at a dosing interval of two to six weeks (i.e., two weeks, three weeks, four weeks, five weeks or six weeks. In a further embodiment, the interval is two weeks).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 2A-2G show immune-tolerance of QPSCs in a xeno-transplanted model. Histopathological findings of the safety test in mice after receiving 3 doses of QPSCs was demonstrated in the figure. No significant lesions of the brain (A), heart (B), kidney (C), liver (D), lung (E), pancreas (F) or spleen (G) were noted in QPSC-treated mice by H&E staining (400×).

FIG. 8 shows QPSCs with the ability of intracranial localization via IV infusion. QPSCs were transplanted into wild type mice via tail vein injection, and brain tissues were removed 7 days after transplantation for quantitative real-time RT-PCR analysis. The ratio of human DNA (detected by human 132 microglobulin) versus mouse DNA (detected by mouse 18s rRNA) was around 0.8% (No. 1 mouse) to 2.8% (No. 4 mouse).

FIGS. 9A-9B shows QPSCs with the ability to differentiate into Purkinje neuron-like cells in the cerebellum of SCA mice. A: One month after three systemic (IV) administration of QPSCs, some of the transplanted cells differentiated into Purkinje neuron-like cells with long axon structure (arrow) in cerebellum of SCA mice. B: Neuron differentiation from QPSC was not found in cerebellum of SCA mice via three intracranial (IC) injections.

FIG. 13 shows that the cell number of SVG p12 was significantly decreased after MPP treatment and this phenomenon was reversed when SVG p12 cells were co-cultured with tenfold amount of QPSCs.

DETAILED DESCRIPTION OF THE INVENTION

Figure 1A:
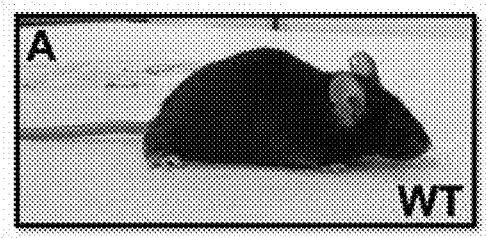
FIGS. 1A-1D shows the appearance and behavior of SCA3 mice.
Figure 1B:
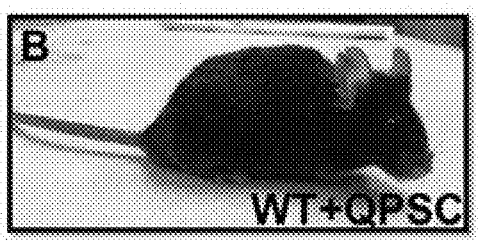
Figure 1C:
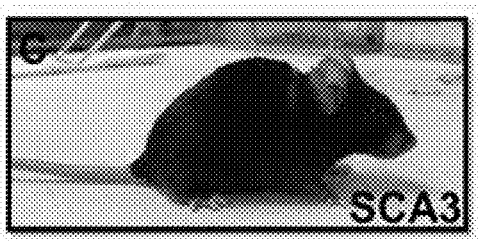
Figure 1D:
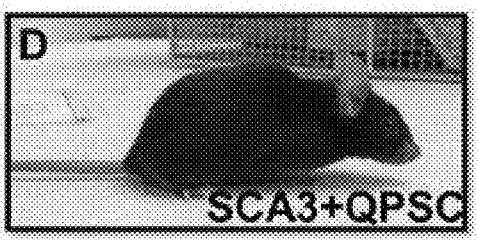

Provided are methods and articles of manufacture for use in stem cell therapy, for the treatment of diseases or conditions of polyQ diseases. The polyQ diseases are a group of neurodegenerative disorders caused by expanded cytosine-adenine-guanine (CAG) repeats encoding a long polyQ tract in the respective proteins. PolyQ diseases are characterized by the pathological expansion of CAG trinucleotide repeat in the translated region of unrelated genes. The translated polyQ is aggregated in the degenerated neurons leading to the dysfunction and degeneration of specific neuronal subpopulations. The invention surprisingly found a treatment regimen with stem cells, which provides an effective therapy for restoration of the functions of degenerative and/or damaged neurons in polyQ diseases.

Unless otherwise noted, technical terms are used according to conventional usage.

As used herein, the singular forms "a," "an," and "the," refer to both the singular as well as plural, unless the context clearly indicates otherwise.

As used herein, the terms "and" and "or" may be used to mean either the conjunctive or disjunctive. That is, both terms should be understood as equivalent to "and/or" unless otherwise stated.

As used herein, the term "treatment," "treat" or "treating" refers to complete or partial amelioration or reduction of a disease or condition or disorder, or a symptom, adverse effect or outcome, or phenotype associated therewith. Desirable effects of treatment include, but are not limited to, preventing occurrence or recurrence of disease, alleviation of symptoms, diminishing any direct or indirect pathological consequences of the disease, decreasing the rate of disease progression, and ameliorating palliating of the disease state.

As used herein, the term "delaying development of a disease" means to defer, hinder, slow, retard, stabilize, suppress and/or postpone development of the disease. This delay can be of varying lengths of time, depending on the history of the disease and/or individual being treated.

As used herein, the term "effective amount" of an agent, e.g., a pharmaceutical formulation, cells, or composition, in the context of administration, refers to an amount effective, at dosages/amounts and for periods of time necessary, to achieve a desired result.

As used herein, the term "therapeutically effective amount" of an agent, e.g., a pharmaceutical formulation or cells, refers to an amount effective, at dosages and for periods of time necessary, to achieve a desired therapeutic result, such as for treatment of a disease, condition, or disorder, and/or pharmacokinetic or pharmacodynamic effect of the treatment.

As used herein, "first dose" is used to describe the timing of a given dose being prior to the administration of a consecutive or subsequent dose. The term does not necessarily imply that the subject has never before received a dose of cell therapy or even that the subject has not before received a dose of the same cells.

As used herein, the term "subsequent dose" refers to a dose that is administered to the same subject after the prior, e.g., first, dose without any intervening doses having been administered to the subject in the interim.

As used herein, the term "subject" is a mammal, such as a human or other animal, and typically is human. In some embodiments, the subject has been treated with a therapeutic agent targeting the disease or condition prior to administration.

As used herein, the term "pharmaceutical formulation" refers to a preparation which is in such form as to permit the biological activity of an active ingredient contained therein to be effective, and which contains no additional components which are unacceptably toxic to a subject to which the formulation would be administered.

As used herein, the term "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

In one aspect, the invention provides a method for treating a polyglutamine (polyQ) disease in a subject, comprising parenterally or locally administering an effective amount of stem cells as a unit dosage to a subject, wherein the administration is performed with one or more treatment cycles, wherein one treatment cycle comprises dosing three unit dosages each at a dosing interval of two to six weeks.

In some embodiment, the polyQ diseases include, but are not limited to, spinocerebellar ataxias (SCA); Machado-Joseph disease (MJD/SCA3); Huntington's disease (HD); dentatorubral pallidoluysian atrophy (DRPLA); and spinal and bulbar muscular atrophy, X-linked 1 (SMAX1/SBMA).

In some embodiments, the SCA is polyglutamine (poly Q)-mediated SCA, Preferably, the SCA is SCA1, SCA2, SCA3, SCA6, SCAT or SCA17. More preferably, the SCA is SCA3.

In some embodiments, the mesenchymal stem cells are mesenchymal stem cell population (MSC), adipose tissue-derived stem cell (ADMSC) population, orbital fat-derived stem cell (OFSC) population or quadri-positive stromal cell (QPSC) population. In one embodiment, the QPSCs are those described in U.S. application Ser. No. 14/615,737, which has at least 70% cell homogeneity and expresses cell markers of CD273, CD46, CD55 and CXCR4 but not CD45; wherein CD273 is strongly expressed at an intensity of over 70%. In one embodiment, the ADSCs are those OFSCs described in US 20120288480, which express at least CD90, CD 105, CD29, CD44, CD49b, CD49e, CD58 and HLA-ABC but do not express CD133, CD31, CD106, CD146, CD45, CD14, CD117. Preferably, the stem cell is QPSC population.

In some embodiments, the cells can be administered by parenteral administration or local treatment (such as intrabrain or intracranial administration). Parenteral infusions include intramuscular, intravenous, intraarterial, or subcutaneous administration. Preferably, the parenteral administration is intravenous injection.

In some embodiments, the unit dosage ranges from $0.5 \times 10^5$ to $5 \times 10^{10}$ cells/kg body weight. In some embodiments, the unit dosage ranges from $0.5 \times 10^5$ to $5 \times 10^9$, $0.5 \times 10^5$ to $5 \times 10^8$, $0.5 \times 10^5$ to $5 \times 10^7$, $0.5 \times 10^5$ to $5 \times 10^6$, $1.0 \times 10^5$ to $5 \times 10^{10}$, $1.0 \times 10^5$ to $5 \times 10^9$, $1.0 \times 10^5$ to $5 \times 10^8$, $1.0 \times 10^5$ to $5 \times 10^7$ or $1.0 \times 10^5$ to $5 \times 10^6$, cells/kg body weight cells/kg body weight.

In one embodiment, the administration is performed with one or more treatment cycles, wherein one treatment cycle comprises three unit dosages each at a dosing interval of two to six weeks (i.e., two weeks, three weeks, four weeks, five weeks or six weeks. In a further embodiment, the interval is two weeks). The number of treatment cycles of the invention is determined according to scale for the assessment and rating of ataxia (SARA) (Subramony S H, SARA—a new clinical scale for the assessment and rating of ataxia. Nat Clin Pract Neurol. 2007; 3(3):136-7; Kim B R, Lim J H, Lee S, Park S, Koh S E, Lee I S, Jung H, Lee J. Usefulness of the Scale for the Assessment and Rating of Ataxia (SARA) in Ataxic Stroke Patients. *Ann Rehabil Med.* 2011; 35: 772-780; and Tan S, Niu H X, Zhao L, et al. Reliability and validity of the Chinese version of the Scale for Assessment and Rating of Ataxia. *Chin Med J.* 2013; 126(11):2045-8). SARA is a clinical scale that is based on a semi-quantitative assessment of cerebellar ataxia (spinocerebellar, Friedreich's and sporadic ataxia) on an impairment level. SARA is an 8-item performance based scale, yielding a total score of 0 (no ataxia) to 40 (most severe ataxia). The scores are based on patient performance of gait, stance, sitting, speech disturbance, finger chase, nose-finger test, fast alternating hand movements and heel-shin slide. After the first treatment cycle, the second and the subsequent treatment cycle are to be performed if the subject maintains total SARA score higher than 5 for one month.

The unit dosage of the stem cells is administered at an interval of two to six weeks. The interval of two to six weeks is meant that a unit dosage of stem cells is administered once in two, three, four, five or six weeks. In one embodiment, the dosing interval is bi-weekly. In one embodiment, the bi-weekly dosing is meant that a unit dosage of stem cells is administered once two-week, i.e. one time during a 14-day period, preferably on the same day of every two weeks. In the bi-weekly dosing regimen, the unit dosage is generally administered about every 14 days.

In the context of stem cell therapy, administration of a unit dosage encompasses administration of the given amount or number of cells as a single composition and/or single uninterrupted administration, e.g., as a single injection or continuous infusion.

In some embodiments, the cells are administered as part of a combination treatment, such as simultaneously with or sequentially with, in any order, another therapeutic intervention. The stem cells in some embodiments are co-administered with one or more additional therapeutic agents or in connection with another therapeutic intervention, either simultaneously or sequentially in any order. In some contexts, the additional therapeutic agents or another therapy are co-administered with cells sufficiently close in time such that the additional therapeutic agents or another therapy enhance the effect of the cell populations, or vice versa. In some embodiments, the stem cells are administered prior to the one or more additional therapeutic agents. In some embodiments, the stem cells are administered after the one or more additional therapeutic agents.

The stem cells used in the method of the invention are formulated as a pharmaceutical composition or formulation, such as unit dose form compositions including the number of cells for administration in a given dose or fraction thereof. The pharmaceutical compositions and formulations generally include one or more optional pharmaceutically acceptable carrier or excipient. In some embodiments, the composition includes at least one additional therapeutic agent.

The choice of carrier is determined in part by the particular stem cell and/or by the method of administration. Accordingly, there are a variety of suitable formulations. For example, the pharmaceutical composition can contain preservatives.

Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG).

Buffering agents in some aspects are included in the compositions. Suitable buffering agents include, for example, citric acid, sodium citrate, phosphoric acid, potassium phosphate, and various other acids and salts. In some aspects, a mixture of two or more buffering agents is used. Methods for preparing administrable pharmaceutical compositions are known.

The formulations can include aqueous solutions. The formulation or composition may also contain more than one active ingredient useful for the particular indication, disease, or condition being treated with the stem cells.

The pharmaceutical composition in some embodiments contains the stem cells in amounts effective to treat the disease or condition, such as a therapeutically effective amount. Therapeutic efficacy in some embodiments is monitored by periodic assessment of treated subjects. The desired dosage can be delivered by a single bolus administration of the cells, by multiple bolus administrations of the cells, or by continuous infusion administration of the cells.

The stem cells and compositions may be administered using standard administration techniques, formulations, and/or devices. Administration of the stem cells can be autologous or heterologous.

Sterile injectable solutions can be prepared by incorporating the cells in a solvent, such as in admixture with a suitable carrier, diluent, or excipient such as sterile water, physiological saline, glucose, dextrose, or the like. The compositions can contain auxiliary substances such as wetting, dispersing, or emulsifying agents (e.g., methylcellulose), pH buffering agents, gelling or viscosity enhancing additives, preservatives, flavoring agents, and/or colors, depending upon the route of administration and the preparation desired. Standard texts may in some aspects be consulted to prepare suitable preparations.

Various additives which enhance the stability and sterility of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, and sorbic acid. Prolonged absorption of the injectable pharmaceutical form can be brought about by the use of agents delaying absorption, for example, aluminum monostearate and gelatin.

EXAMPLE

Figure 15A:
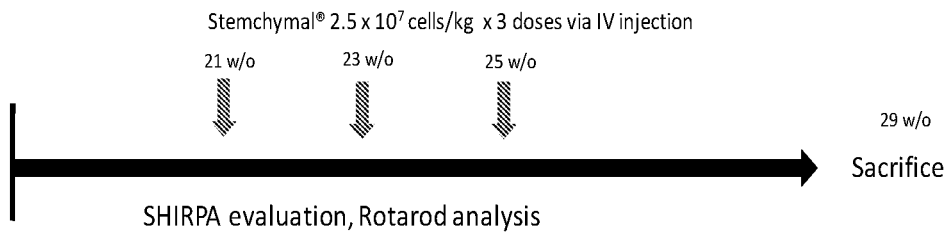
FIG. 15A shows the study design in mice without significant motor function deterioration and FIG. 15B shows the study design in mice with significant motor function deterioration.

I. Animal Model Trial
Materials and Methods
Animals and Experimental Design
Mice without Significant Motor Function Deterioration MJD84.2 (B6;CBA-Tg(ATXN3*)84.2Cce/IbezJ) mice have been established as a disease model for human Machado-Joseph disease, also known as spinocerebellar ataxia type 3 (MJD/SCA3). In this study, MJD84.2 animals, ranging from ages of 20-34 weeks, were studied. Behavioral analyses including modified—SHIRPA, footprint analysis, and rotarod tests were performed on these animals. Three test article injections at an interval of two-weeks were carried out in mice aged 21, 23 and 25 weeks. The study design is outlined in FIG. 15A.

Mice with Significant Motor Function Deterioration

Figure 15B:
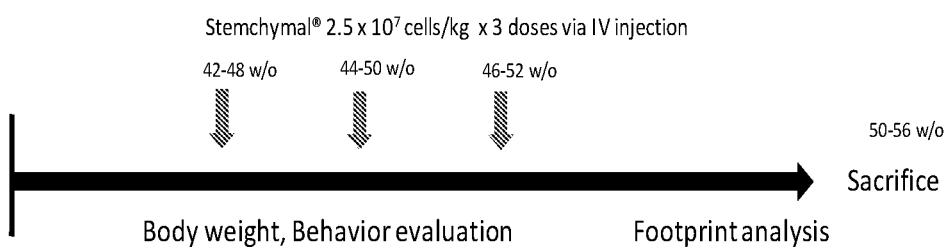

A total of thirteen SCA3 Tg/0 mice (B6;CBA-Tg(ATXN3*)84.2Cce/IbezJ) and eight C57BL/6 0/0 wild type mice were originally from JAX Laboratory. Animals were randomly enrolled into four experimental groups: (1) SCA3+ cells; (2) SCA3+PBS; (3) Wt+ cells; (4) Wt+PBS. Three test article injections at an interval of two-weeks were carried out after significant disease phenotype in SCA3 Tg/0 mice was determined. The study design is outlined in FIG. 15B.

Mesenchymal Stem Cells

QPSCs in this study are human ADMSCs (Stemchymal®), a cell product manufactured by Steminent Biotherapeutics Inc. (SBI). ADMSCs were ex-vivo culture expanded and quality controlled followed SBI's standard operation procedures in a cell factory established in accordance with PIC/S Good Manufactory Practice guideline. In brief, adipose tissue was harvested from healthy donors and immediately transported to SBI's processing facility in low temperature (0~5° C.). ADMSCs were isolated, purified and maintained in SBI's proprietary culture medium during culture expansion. ADMSCs with passage at 12 were QPSCs with highly expressed CD273, CD46, CD55 and CXCR4, then packaged in a cryopreservation bag, and the product (Stemchymal®) was sent for quality certification and cryopreservation. The quality control for Stemchymal® is composed of in-process control and product-release tests, which includes but are not limited to viability, sterility, mycoplasma tests, endotoxin assessment, MSC phenotyping (positive for CD 73, CD 90, and CD 105, negative for CD 34, CD 45, CD11b, CD 19 and HLA-DR), and tri-lineage differentiation capacity (osgeogenic, chondrogenic and adipogenic differentiation).

Cell Dosing
For Study Using Mice without Significant Motor Function Deterioration:

$2.5 \times 10^7$ cell/kg bodyweight of Stemchymal® was thawed, prepared and loaded into 1 ml insulin syringe (29½G). Cells were injected slowly (15-20 second duration) within one hour of thawing.

For Study Using Mice with Significant Motor Function Deterioration:

Mice were randomly distributed into 4 groups: (1) SCA3+ cells, (2) SCA3+PBS, (3) Wt+ cells, (4) Wt+PBS. $2.5 \times 10^7$ cell/kg bodyweight of Stemchymal® was intravenously infused to each mouse in group 1 and 3. A total of 125 ul of cell suspension (1:1 in cryosolution (Biolife)) or PBS (Gibco) was administered to each mouse.

For both studies, animals were monitored for 4 hours and observed daily after injection. Cell dosing was carried out once every two weeks, a total of three times.

Data Collection & Analysis

Mice were sacrificed one month after the last test article injection. Body weight and latency to fall of mice were recorded for the entire study. Mouse footprints were also analyzed for gait performance after test article injection. Mice tissues (cortex, cerebellum, heart, kidney, liver, spleen, lung and tail) were collected for future histopathologic analysis and bio-distribution study.

Statistics

Data are presented as mean±SEM. Results of Rotarod and Footprint tests were analyzed using Student's t-test with a significance threshold of $p<0.05$.

Motor Coordination and Balance Assay

Motor coordination and balance were evaluated in a rotarod apparatus (MK-670, Muromachi Kikai Co., Ltd., Japan). Mice were placed on the rotarod at a constant speed (4 rpm) that accelerated to 40 rpm over a 5 min period. The latency to fall or to complete a full passive rotation (clinging on the rod for a full rotation) was recorded. Mice were allowed to perform 3 trials for each test, with 15 min rest between trials. The average latency for each mouse from each test were calculated. Test results were statistically analyzed using t-test.

SHIRPA Test

Modified SHIRPA tests were performed at 20, 24 and 28 weeks of mouse age. SHIRPA protocol was modified from RIKEN BRC's modified SHIRA protocol. Test items and scoring criteria are listed in the following table.

| Test items | Score |
|---|---|
| Transfer arousal | 0 = Coma |
| | 1 = Normal movement, <5 squares |
| | 2 = Normal movement, 5~15 squares |
| | 3 = Normal movement, >15 squares |
| | 4 = Abnormally fast movement |
| | 5 = Abnormally fast movement without pause |
| Pelvic elevation | 0 = Markedly flattened (pelvis completely touches the floor) |
| | 1 = Barely touches (pelvis less than 3 mm above the floor) |
| | 2 = Normal (pelvis 3 mm above the floor) |
| | 3 = Elevated (pelvis more than 3 mm above the floor) |
| Wire maneuver | 0 = Securely grips with a hindlimb (for 5 sec ) |
| | 1 = Difficulty gripping with a hindlimb |
| | 2 = Unable to grip with a hindlimb |
| | 3 = Unable to lift a hindlimb, falls within seconds |
| | 4 = Falls immediately |
| Ledge test | 0 = In balance, lower itself to the arena |
| | 1 = Loses footing while walking |
| | 2 = Difficulty using hind legs, head dive when lower to the arena |
| | 3 = Falls off or cannot move |
| | 4 = Does not move |
| Negative geotaxis | 0 = Turns and climbs the grid |
| | 1 = Turns, then freezes |
| | 2 = Moves, but fails to turn |
| | 3 = Does not move within 30 seconds |
| | 4 = Falls |

Mice were scored according to their behaviors. Total mouse number in the study group was calculated as 100%. Results were presented as percentage of mouse number with certain scoring levels.

Footprint Analysis

Mouse footprint was analyzed around one month after the last cell dosing. Referring to paper published in 2015 (1), mouse paws were dipped in inks (Fore: red; Hind: green), so that the mice leave a trail of footprints as they walk or run along a corridor to a goal box. Mice were placed on a sheet of paper (50-cm-long, 10-cm-wide) in front of a tunnel. Measurements of stride, sway, stance length, and fore and hind paw overlap give an indication of gait (see following figure). All mice were given 3 runs before sacrifice.

MTT Assay $CD3^+$ T Cell Isolation

Human peripheral blood mononuclear cells (PBMCs) were isolated from heparinized whole blood from healthy donors by Histopaque-1077(Sigma-Aldrich) density gradient centrifugation. $CD3^+$ T lymphocytes were then purified by positive selection from PBMCs using anti-human CD3 antibody conjugated magnetic particles (BD Biosciences) following the manufacturer's instructions.

T Cell Proliferation Assay

Purified human $CD3^+$ T cells ($1\times10^5$ cells) were stimulated with plate-bound anti-CD3 (2 µg/ml) and anti-CD28 (2 µg/ml) monoclonal antibodies (BD Biosciences) in 96-well plate and co-cultured with different numbers of ADMSCs in RPMI-1640 medium (Gibco) containing 10% fetal bovine serum (FBS), 2 mM 1-glutamine, 100 U/ml penicillin, 100 U/ml streptomycin and 25 mM HEPES. After 48 hours, 5-bromo-2-deoxyuridine (BrdU) was added to each well and the plate was incubated for another 18 hours for measurement of T cell proliferation. The amount of BrdU incorporated into the T cells was measured using the Cell Proliferation ELISA, BrdU kit (Roche) according to the manufacturer's instructions.

Immunohistochemistry (IHC)

To evaluate the neuroprotective effects of QPSCs, QPSCs were injected via tail vein (IV hMSC-Tg group) or through foramen magnum into position of cerebellum (IC hMSC-Tg group), of C57BL/6J SCA2 transgenic mice. Specific antibody which reacted with human beta2 microglobulin (Abeam, code: ab15976) was chosen to demonstrate human cells in murine brain tissue by IHC. Murine sections (4 µm) were cut and mounted onto microscopic slides. Sections were rehydrated by rinsing twice at 5 min intervals in xylene, 100% ethanol, 95% ethanol and 80% ethanol. After deparaffinization, sections were treated with 3% $H_2O_2$ for peroxidase inactivation, heated in 10 mM citrate buffer (with 0.05% Tween20) for antigen retrieval, and blocked with 1% blocking solution (1% BSA and 0.1% Triton X-100 in Chang et al. Journal of Biomedical Science 2011, 18:54 http://www.jbiomedsci.com/content/18/1/54 Page 3 of 9 PBS). Sections were incubated with specific anti-human b2 microglobulin polyclonal antibodies (Abeam) diluted in blocking solution (1:400) for 40 min at RT. After three extensive washes with PBS, sections were incubated with secondary antibody diluted in blocking solution (1:1000) for 40 min at RT. Primary antibodies were detected using EnVision Detection System (DAKO), and visualized with diaminobenzidine (DAB; DAKO). We counterstained with aqueous haematoxylin (SigmaAldrich). For direct comparison we processed all slides in a single batch to minimize variability Safety Test Animals C57BL/6 mice were received 3 doses of QPSCs through intravenous injection at tail using Insulin Syringe ½ cc 30G×⅜" Needle (Terumo, or BD Bioscience). Prior to the injection, animals were warmed by a heat pad placed under the cage for 15-20 minutes to dilate their tail veins. Before necropsy, all animal were anesthetized with urethane (2 g/kg of body weight, Sigma-Aldrich) followed by blood collection from submandibular vein or through cardiac puncture.

Blood Sample Collection

For hematology analysis, the whole blood sample was collected in an EDTA containing blood collection tube (BD Bioscience, Cat No. 365974). For blood chemistry analysis, the whole blood sample was collected in blood collection tube containing serum separator (BD Bioscience, Cat No. 365967). Followed by standing the serum tube in room temperature for 20 min, the serum was then separated by centrifugation at 4° C., 6000 rpm for 5 min.

Gross Necropsy and Tissue Collection

After blood sampling, animal organs were collected. Each of them were divided into two portions: (1) half of the organ was preserved in the −80° C. freezer, then transferred and stored in the liquid nitrogen container for biodistribution analysis; (2) the other half was fixed (4% paraformaldehyde, Sigma-Aldrich) and paraffin embedded for histopathological analysis.

Quantitative PCR

Total RNA from QPSCs or murine tissue was extracted using Total RNA Miniprep Purification Kit (GMbiolab Cat #TR01) following the manufacturer's instructions. Then, a two-step MMLV RT-PCR kit (GMbiolab Cat #RP012-M) was used for cDNA synthesis. Quantitative PCR for the relative expression analysis of selected genes was carried out using The Fast SYBR® Green Master Mix (Thermo Cat #4385612).

ELISA

To measure the intracellular and secretory content of EGF, FGF-b, VEGF, PDGF and TGF-b1 of QPSC, samples of cell lysate and conditioned medium were prepared as follows: QPSC was lysed by using freeze-thaw method, and the supernatant of cell lysate was collected after ultracentrifugation. And for conditioned medium collection, the medium was collected after 3 days QPSCs culture. Lastly, the concentration of above growth factors was determined by ELISA according to the manufacturer's instructions (R&D systems).

Neuronal Cell Coculture Test

A human astrocyte cell line, SVG p12, was treated with 1250 uM 1-Methyl-4-phenylpyridine (MPP+) and co-cultured with different proportion of QPSCs (SVG p12: QPSC=1:0.1~1:10). After 24 hours, cell number of SVG p12 was counted.

Example 1 QPSC Changes the Phenotype of SCA3

Figure 4A:
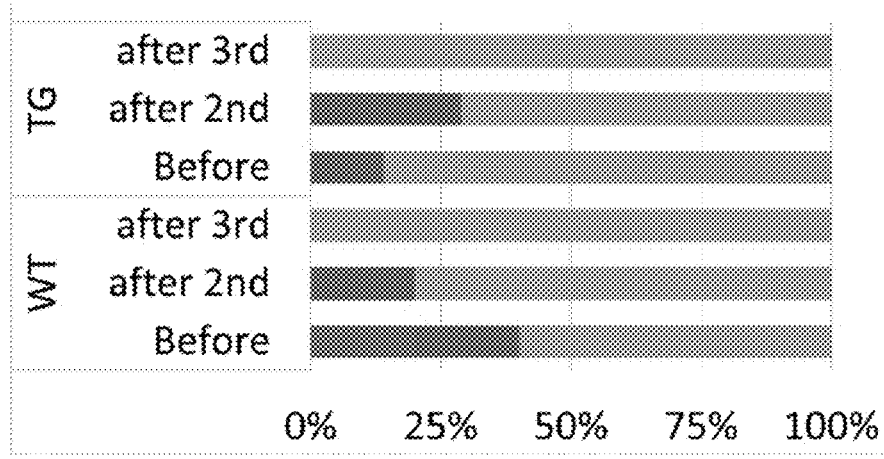
FIGS. 4A-4C show that QPSCs change the phenotype of SCA3 mice. Both WT and SCA3 transgenic mice (TG) received intravenous QPSC administration for three times. Modified SHIRPA was carried out before and after QPSCs treatments. A, the figure illustrated that QPSCs altered the phenotyping of SCA3 mice with pelvic elevation. B and C, QPSCs altered the phenotyping of SCA3 mice in grip strength.
Figure 4B:
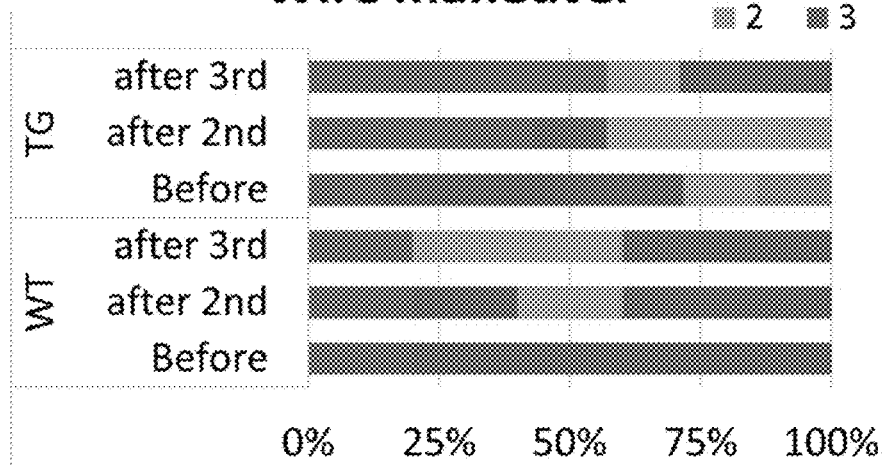
Figure 4C:
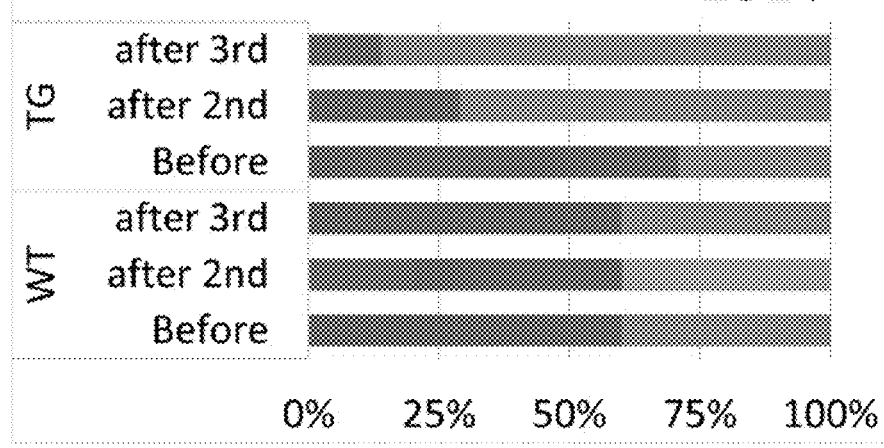
Figure 5A:
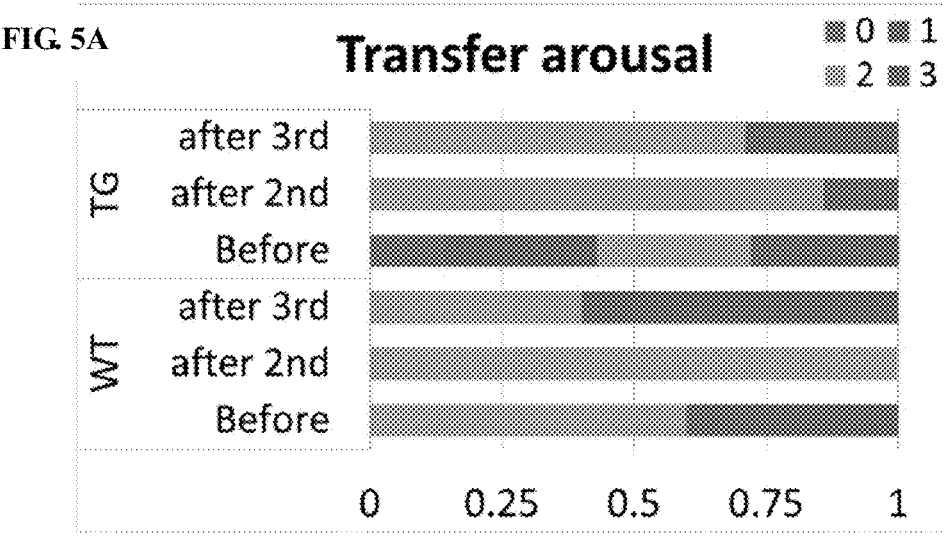
FIGS. 5A-5C show that three doses of QPSCs improve motor function of SCA3 mice without significant motor function deterioration. Both WT and SCA3 transgenic mice (TG) received intravenously QPSC administration for three times. Modified SHIRPA and rotarod performance were carried out before and after QPSCs treatments. A and B: SCA3 mice had an improved movement and negative geotaxis performance after QPSC treatment. C: a significant improvement on rotarod performance of SCA3 mice (Tg) after 3 doses of QPSC infusions.
Figure 5B:
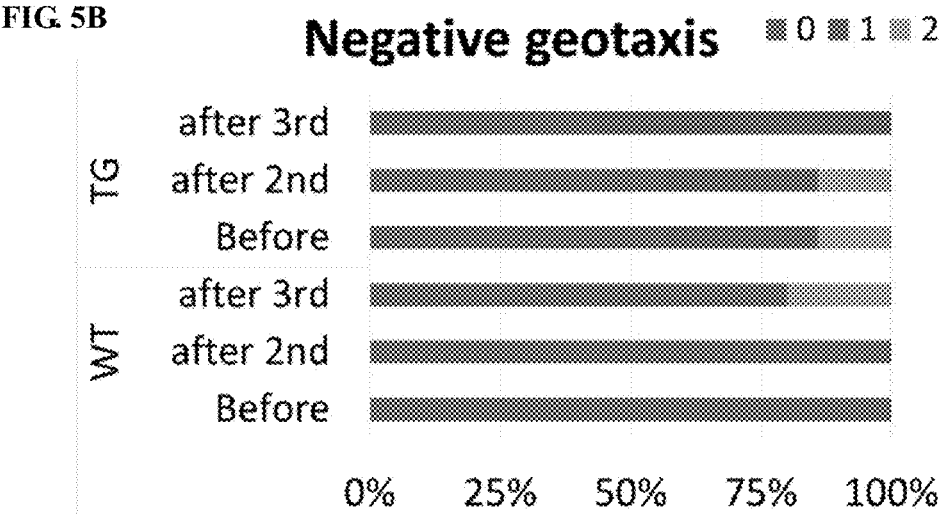
Figure 5C:
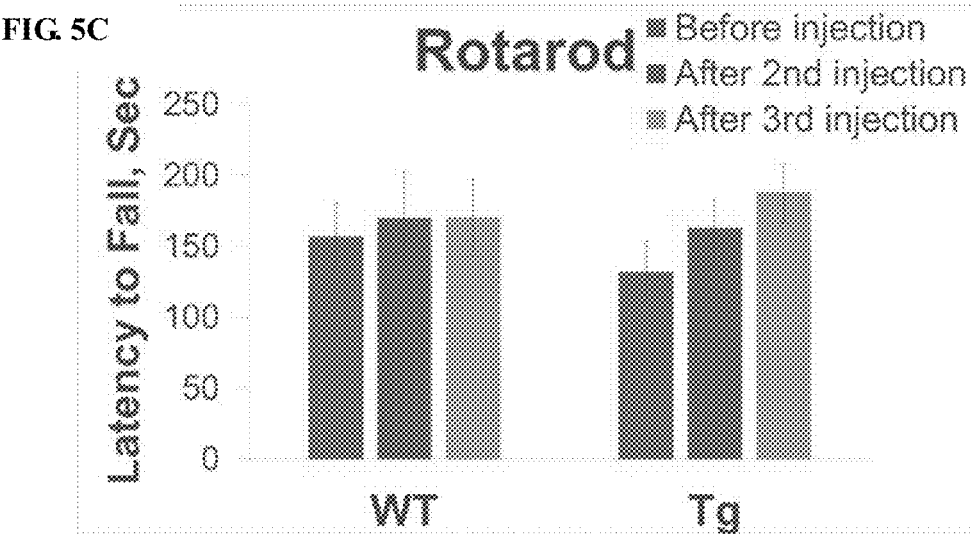
Figure 6A:
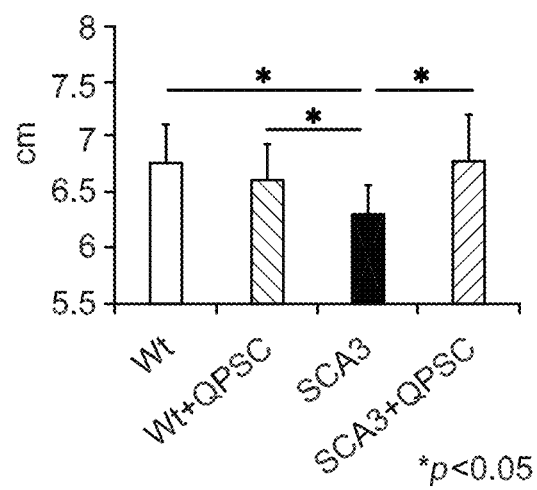
FIGS. 6A-6D show that three doses of QPSCs improves motor function of SCA3 mice with significant motor function deterioration. Footprint analysis on mice was performed one month after the third QPSC injection. A-D, The figures show that SCA mice presented a reduced footprint-Stride distance in left fore foot (L.F.) (A), right fore foot (R.F.) (B), left hind foot (L.H.) (C) and right hind foot (R.H.) (D), and 3 does of QPSCs rescued the impaired stride distance.
Figure 6B:
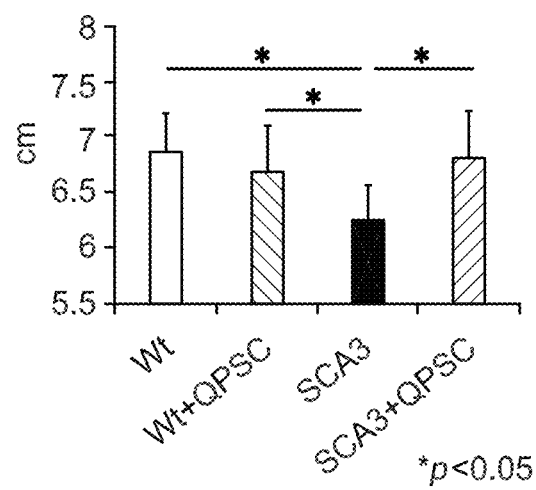
Figure 6C:
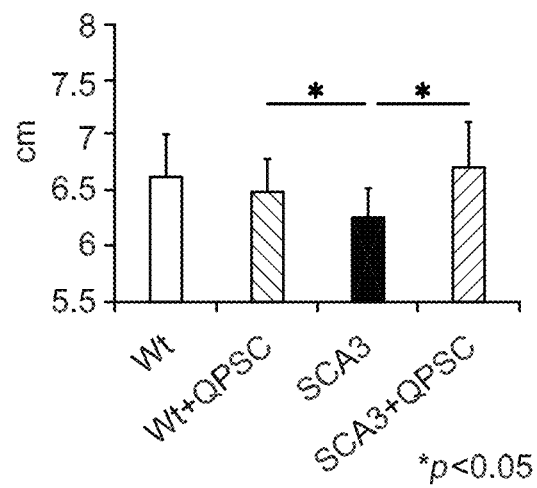
Figure 6D:
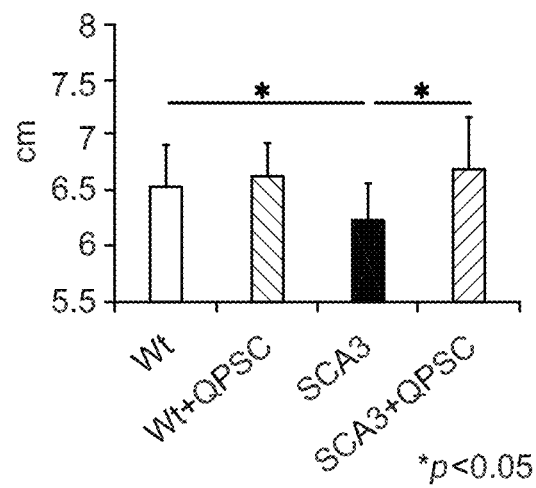
Figure 7A:
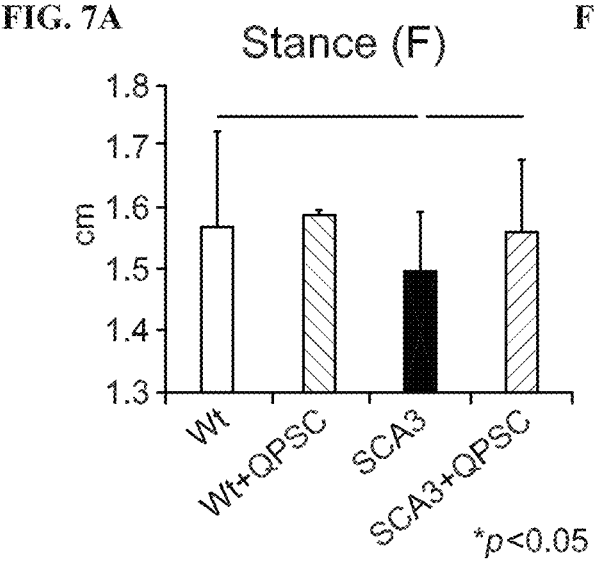
FIGS. 7A-7D show that three doses of QPSCs improves gait balance of SCA3 mice. Footprint analysis on mice was performed one month after the third QPSC injection. A-D: A and B show footprint-Stance in fore (F) and hind (H) feet of mice, respectively, while C and D show footprint-overlap in left (L) and right (R) feet of mice. Three doses of QPSCs note only rescued the impaired stance distance attacked by SCA, but also kept the footprint overlap near 100% overlapping.
Figure 7B:
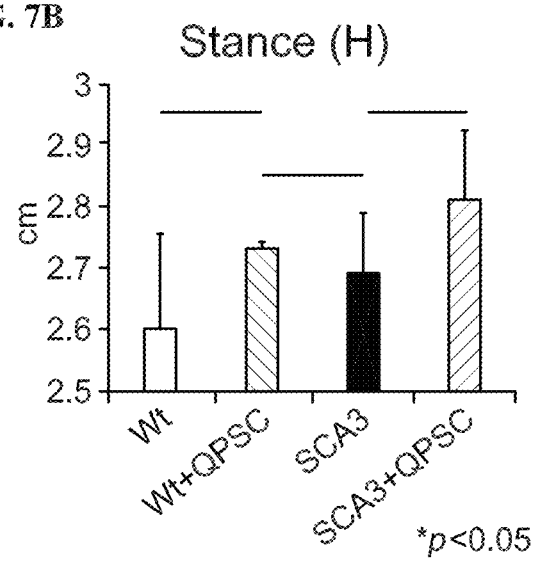
Figure 7C:
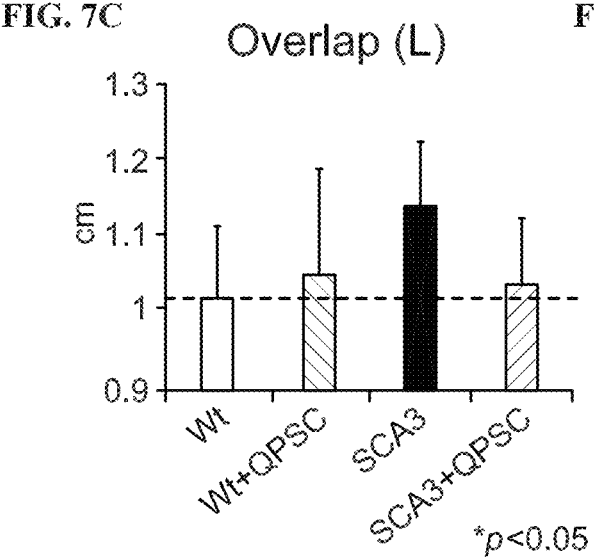
Figure 7D:
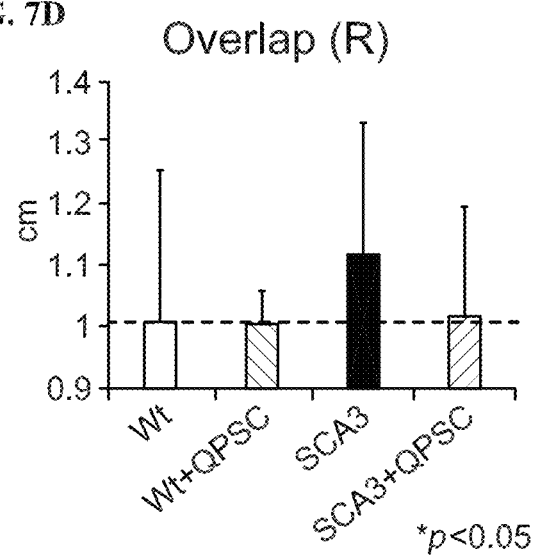

QPSC changed the phenotype of SCA3 mice. As shown in FIG. 1, SCA3 mice show a slightly wider base compared to wild type mice and after QPSC treatment, the appearance of SCA3 mice looked similar to that of wild type mice. Similar improvement result was observed in various functional tests, such as modified SHIRPA (FIG. 4, 5), footprint (FIG. 6, 7) and rotarod performance analysis (FIG. 5C).

Figure 3A:
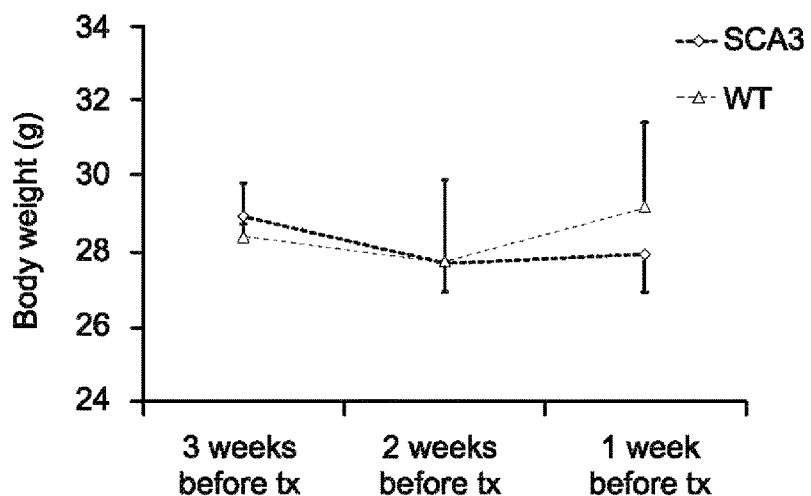
FIGS. 3A-3C show that QPSCs stop body weight loss of SCA3 mice. Body weight was recorded weekly before QPSC treatment and bi-weekly after QPSC treatment. Animals were sacrificed one month after the $3^{rd}$ QPSC injection. A, SCA3 mice had a reduced body weight compared to wild type mice before QPSC treatment. B and C, QPSC prevented body weight loss in SCA3 mice.
Figure 3B:
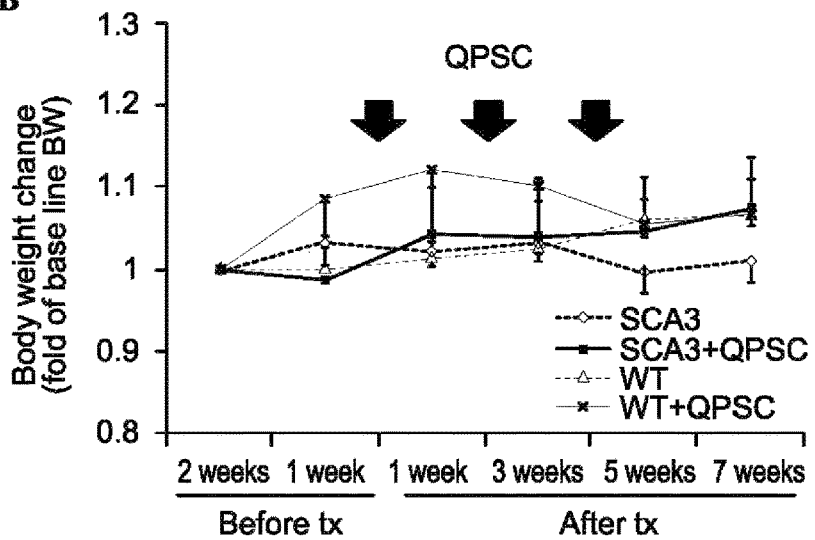
Figure 3C:
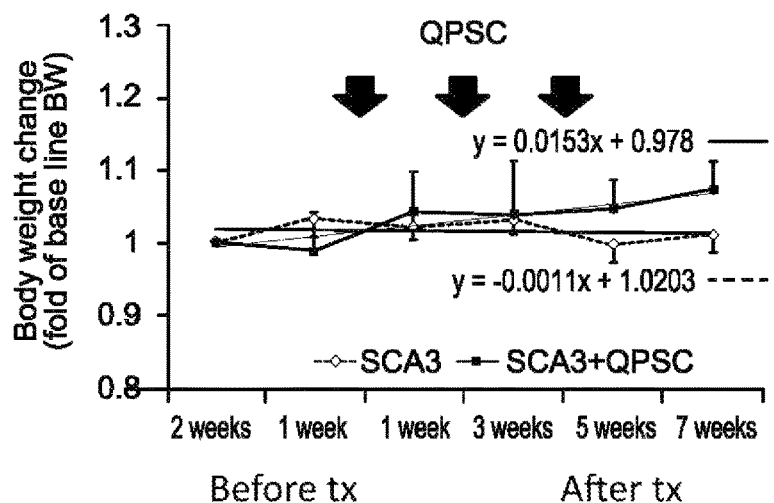

Example 2 Stop of Body Weight Loss and No Side Effect in Organ Tissues by the Treatment of the Invention QPSC also stopped the body weight loss of SCA3 during the progress of disease (FIG. 3). Nevertheless, 3 doses of QPSCs did not affect the profile of complete blood count (Table 1) or blood biochemistry (Table 2) in SCA3 individual. Tables 1 and 2 show no difference of complete blood count/biochemistry profile from wild type mice aged at 25-30 weeks between three doses of QPSCs and saline for three doses at an interval of one week. Histopathological analysis showed normal findings in various vital organ tissues after 3 doses of QPSC injections (FIG. 2).

TABLE 1

| | | Treatment Age | | |
|---|---|---|---|---|
| Item | Unit | Saline x3 (one-week interval) 25-30 wks | QPSC x 3 (one-week interval) 25-30 wks | P value |
| WBC count | $\times 10^3/\mu L$ | 3.43 ± 1.74 | 3.70 ± 1.09 | 0.863 |
| NEU count | $\times 10^3/\mu L$ | 0.43 ± 0.34 | 0.35 ± 0.17 | 0.774 |
| LYM count | $\times 10^3/\mu L$ | 2.92 ± 1.39 | 3.22 ± 0.87 | 0.812 |
| MONO count | $\times 10^3/\mu L$ | 0.03 ± 0.02 | 0.05 ± 0.01 | 0.185 |
| EOS count | $\times 10^3/\mu L$ | 0.05 ± 0.03 | 0.08 ± 0.04 | 0.465 |
| BASO count | $\times 10^3/\mu L$ | 0.00 ± 0.00 | 0.01 ± 0.01 | 0.272 |
| NEU % value | % | 11.10 ± 4.51 | 9.20 ± 1.84 | 0.625 |
| LYM % value | % | 86.23 ± 3.66 | 87.20 ± 2.12 | 0.765 |
| MONO % value | % | 1.17 ±1.25 | 1.35 ± 0.07 | 0.857 |
| EOS % value | % | 1.50 ± 0.17 | 2.10 ± 0.57 | 0.162 |
| BASO % value | % | 0.00 ± 0.00 | 0.15 ± 0.21 | 0.272 |
| RBC count | $\times 10^6/\mu L$ | 10.91 ±0.27 | 10.63 ± 0.37 | 0.390 |
| HGB value | g/dL | 15.50 ± 0.44 | 14.95 ± 0.35 | 0.238 |
| HCT value | % | 54.20 ± 1.47 | 52.75 ± 2.19 | 0.430 |
| MCV value | fL | 49.67 ± 0.46 | 49.65 ± 0.35 | 0.969 |
| MCH value | pg | 14.20 ± 0.10 | 14.10 ± 0.14 | 0.413 |
| MCHC value | g/dL | 28.60 ± 0.10 | 28.35 ± 0.49 | 0.425 |
| RDW-CV | % | 25.47 ± 0.58 | 25.10 ± 0.57 | 0.534 |
| RET count | $\times 10^3/\mu L$ | 389.50 ± 30.93 | 400.15 ± 69.93 | 0.822 |
| RET value | % | 3.57 ± 0.24 | 3.78 ± 0.79 | 0.675 |
| PLT count | $\times 10^9/L$ | 467.67 ± 444.72 | 787.50 ± 43.13 | 0.407 |
| MPV value | fL | 6.55 ± 0.35 | 6.50 ± 0.00 | 0.860 |
| PCT value | % | 0.44 ± 0.22 | 0.51 ± 0.03 | 0.679 |
| PDW value | fL | 8.20 ± 0.71 | 7.80 ± 0.14 | 0.515 |

Data is presented by Mean ± SD

TABLE 2

| | | Treatment Age | | |
|---|---|---|---|---|
| Item | Unit | Saline x3 25-30 wks | QPSC x 3 25-30 wks | P value |
| GOT | U/l | 70.50 ± 13.44 | 62.50 ± 0.71 | 0.489 |
| GPT | U/l | 19.50 ± 2.12 | 11.50 ± 6.36 | 0.234 |
| GLU | mg/dl | 187.50 ± 13.44 | 201.00 ± 9.90 | 0.371 |
| BUN | mg/dl | 36.60 ± 2.55 | 35.40 ± 6.79 | 0.837 |
| CRE | mg/dl | 0.45 ± 0.07 | 0.40 ± 0.14 | 0.698 |
| TCHO | mg/dl | 82.00 ± 22.63 | 81.50 ± 2.12 | 0.978 |
| TG | mg/dl | 119.00 ± 14.14 | 86.50 ± 45.96 | 0.440 |
| CKMB | mg/dl | 294.50 ± 6.36 | 204.00 ± 35.36 | 0.071 |

Data is presented by Mean ± SD

Figure 10A:
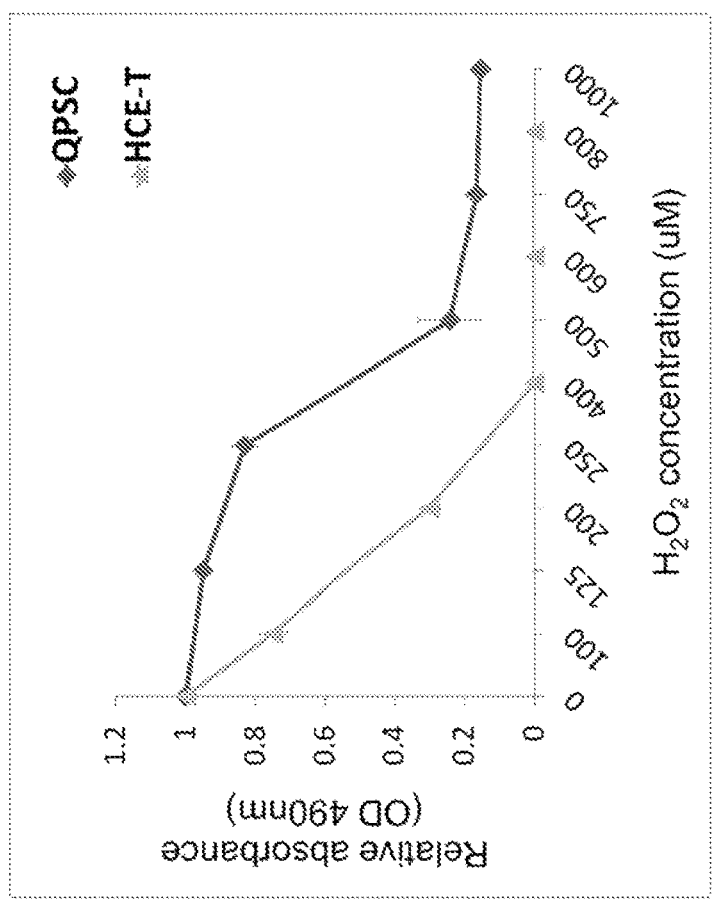
FIGS. 10A-10B show that QPSCs possesses strong immunomodulatory and anti-ROS capacity. A: Human T cell proliferation is stimulated by CD3/28 and this stimulated proliferation is inhibited by co-culture with Stemchymal at all mixture ratios (*** indicates significant difference [$P<0.05$], n=3). B: The anti-$H_2O_2$ ability of QPSCs is 3-fold superior to anti-$H_2O_2$ ability of human conical epithelial cells (HCE-T), cells relatively resistant to oxidative stress.
Figure 10B:
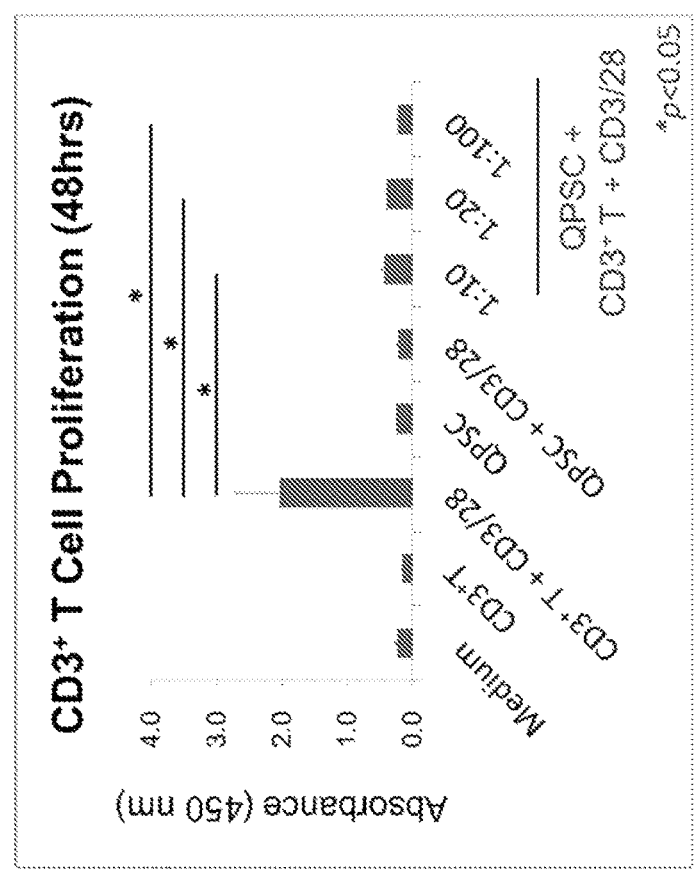
Figure 11A:
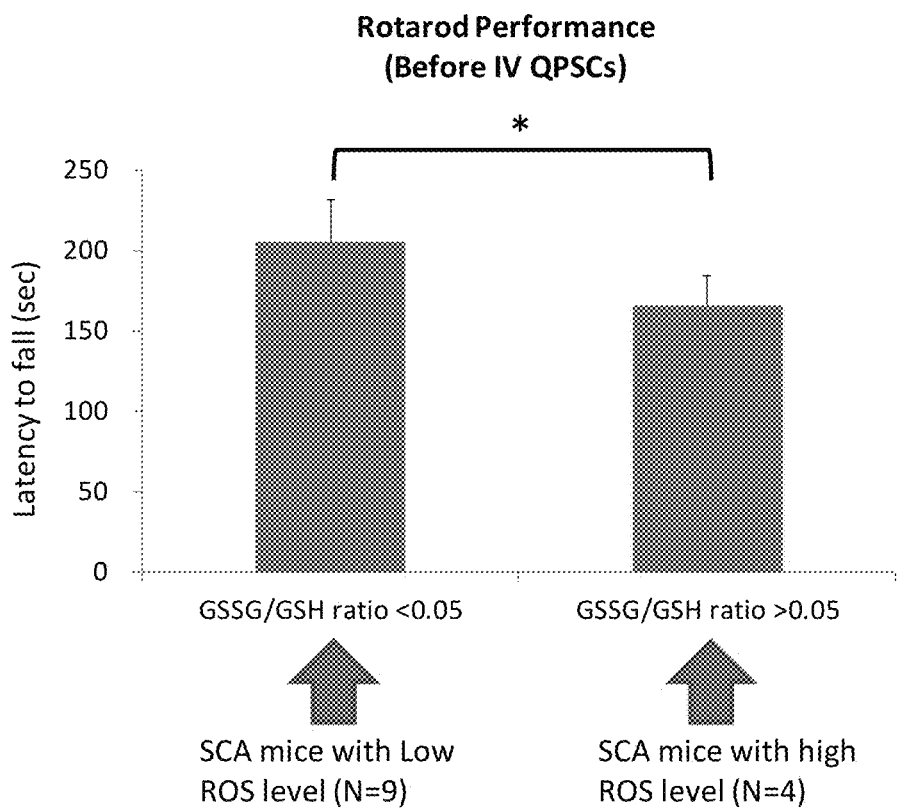
FIGS. 11A-11B show that QPSCs inhibit oxidative stress-related motor function deterioration in SCA mice. A: SCA mice with low oxidative stress (low ROS level) show a better rotarod performance than SCA mice with high oxidative stress (high ROS level). B: Motor function performance deterioration progresses in SCA mice (Tg-Ctrl), while systemic QPSCs transplantation in SCA mice, both with high and low oxidative burden (Tg-QPSCs-high ROS, Tg-QPSCs-low ROS), maintains better Rotard performance compared to Tg-Ctrl especially in Tg-QPSCs-low ROS group (*$P<0.05$). Wild-type mice were compared as normal control (WT-Ctrl).
Figure 11B:
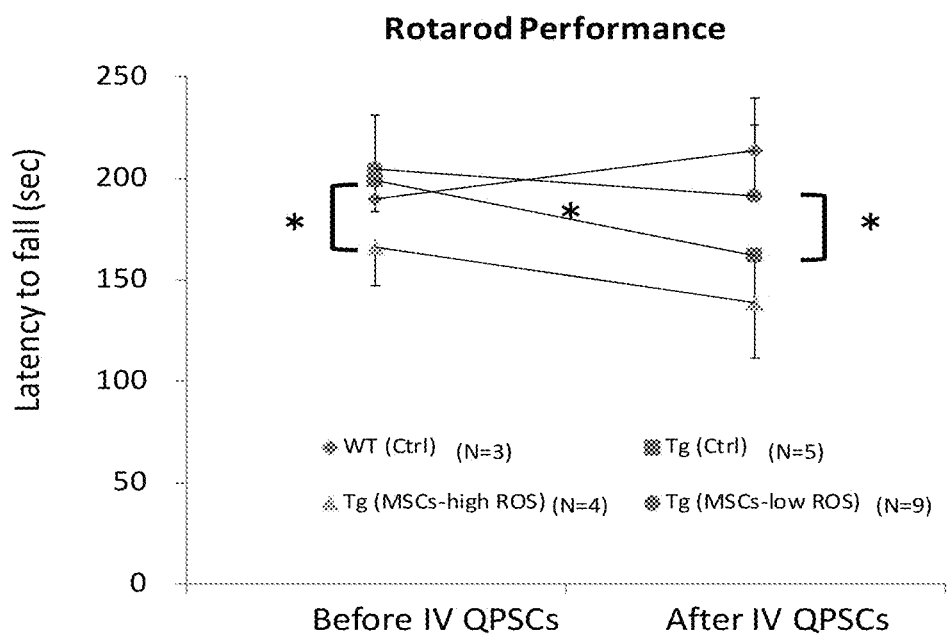
Figure 12A:
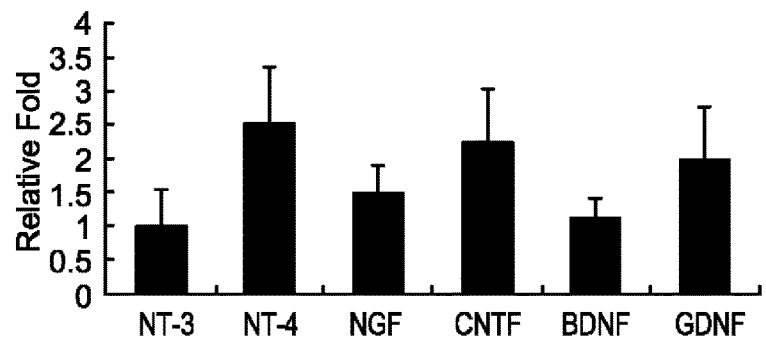
FIGS. 12A-12C shows that QPSCs expresses multiple paracrine neurotrophic factors and tissue growth factors. Gene expression of neurotrophic factors including NT-3, NT-4, NGF, CNTF, BDNF and GDNF in QPSCs were detected by quantitative PCR (qPCR) relative to internal control 18srRNA gene (A). Tissue factors such as EGF, FGF-β and VEGF (B) and PDGF and TGF-β1 (C) in QPSCs were also examined by ELISA, and differential concentrations of those factors between intracellular fraction and secretory fraction were demonstrated.
Figure 12B:
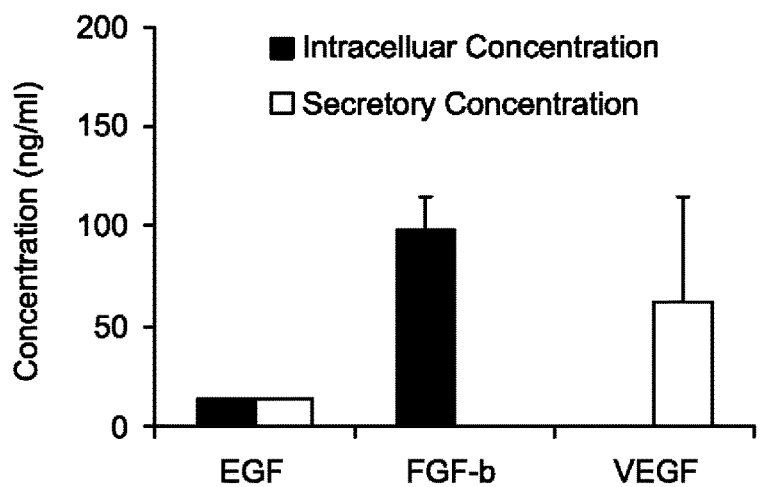
Figure 12C:
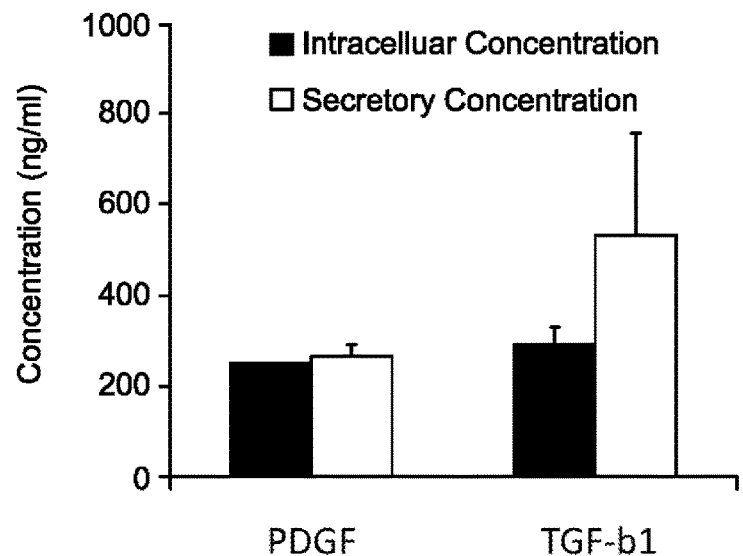
Figure 13:
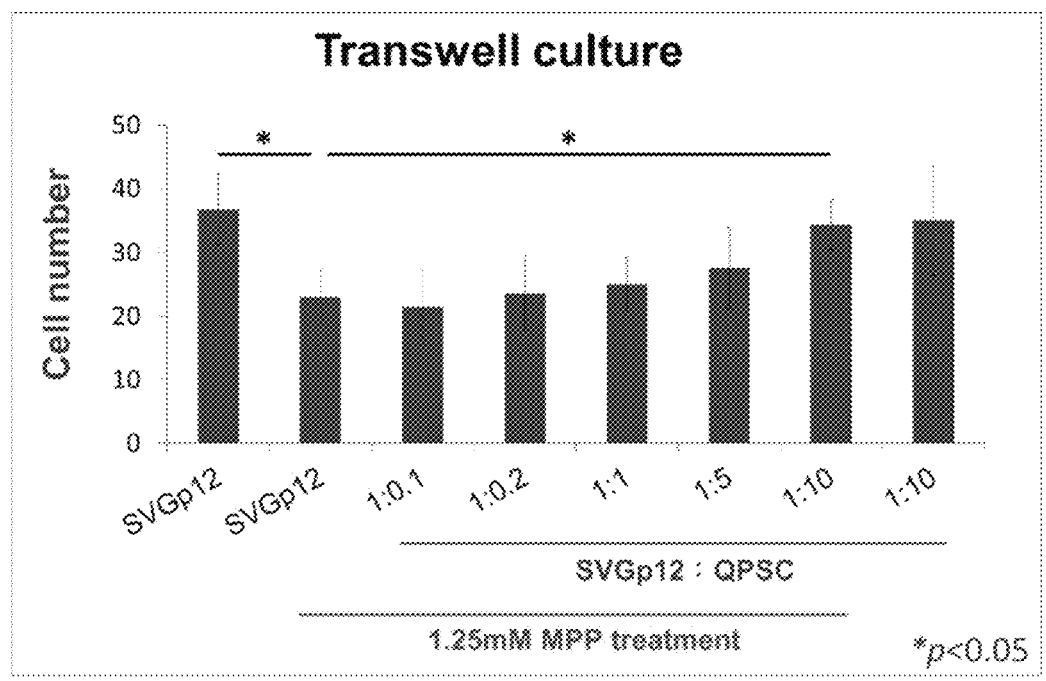
FIG. 13 shows that QPSCs paracrine rescues astrocyte neuron from MPP-induced neuron loss. A human astrocyte cell line, SVG p12, was treated with 1.25 mM 1-Methyl-4-phenylpyridine (MPP+) and co-cultured with different proportions of QPSCs at the same time. After 24 hours of treatment, the cell number of SVG p12 was counted.
Figure 14B:
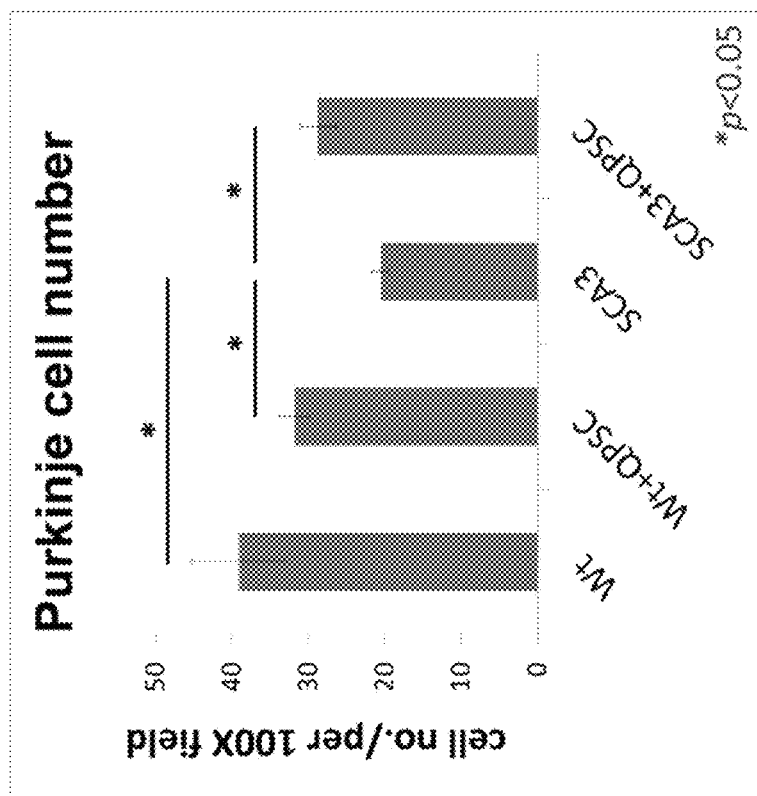
FIGS. 14A-14C show that QPSCs rescue Purkinje neuron loss in the cerebellum of SCA3 mice. Mice cerebellum were collected after sacrifice. Collected tissues were fixed and paraffin-embedded for further histopathological analysis. Tissue sections were stained with hematoxylin and eosin (HE) and immunohistochemistry (IHC) staining targeting Purkinje cells (anti-calbidin, ab11426, abeam). A. Smaller sized and deformed Purkinje cells in cerebellum of SCA3 mice with significant motor function deterioration were observed when comparing to that of wild type mice. B and C, Purkinje cell number in cerebellum was significantly reduced in SCA3 mice, while 3 doses of QPSCs prevented the Purkinje neuronal loss from SCA.
Figure 14A:
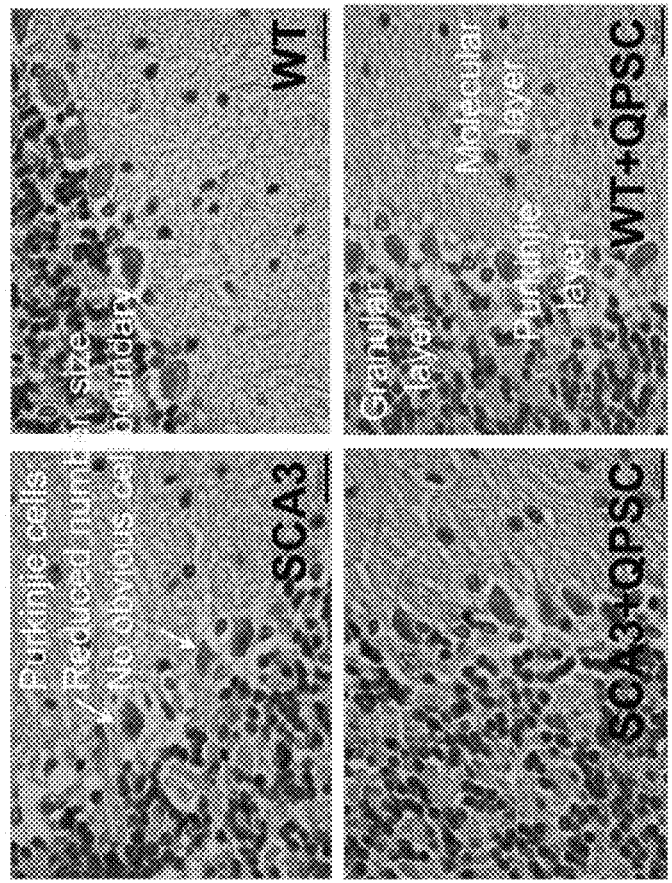
Figure 14C:
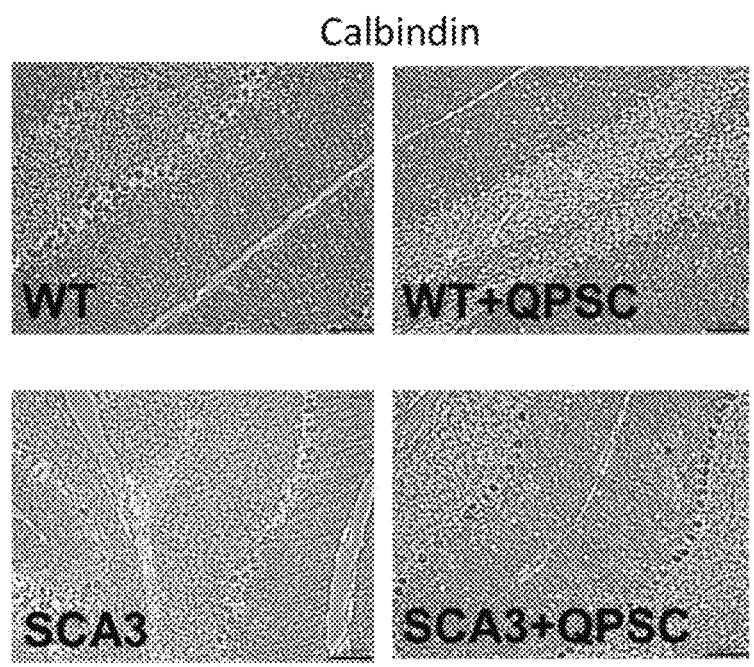

Example 3 Immunomodulatory and Anti-ROS Capacities and Expression of Express Multiple Neurotrophic Factors and Growth Factors in Mice Using the Treatment of the Invention In vitro studies showed that QPSCs not only possessed immunomodulatory and anti-ROS capacities (FIG. 10), but also had the ability to express multiple neurotrophic factors and growth factors (FIG. 12). In vivo study demonstrated the improvement of rotarod performance in SCA mice under oxidative stress after QPSCs treatment (FIG. 11). In addition, QPSCs could prevent neuronal loss both in vitro (FIG. 13) and in vivo (FIG. 14). Although the query of possibility for cells migrating across blood brain barrier (BBB) has been proposed, the ability of intracranial localization via intravenous infusion of QPSCs was demonstrated (FIGS. 8 and 9).

Therefore, it is reasonable to conclude that through intravenous infusion, QPSCs may pass BBB to cerebellum and protect neuron cells in SCA individual from damage of ROS and immune overreaction. QPSCs also secret multiple neurotrophic and growth factors to maintain the number of neuron cells to, therefore, delay the progression of poly-Q diseases such as polyglutamine spinocerebellar ataxia, Machado-Joseph disease, Huntington's disease, DRPLA, and SMAX1/SBMA.

II. Human Clinical Trial

The human clinical trial is to study the therapeutic efficacy and safety of Stemchymal® infusions for treatment of polyglutamine-mediated diseases (such as polyglutamine spinocerebellar ataxia, Machado-Joseph disease, Huntington's disease, DRPLA, and SMAX1/SBMA) by a randomized, double-blind, placebo-controlled study design. Eligible subjects will receive Stemchymal® through intravenous infusion.

In one example for polyglutamine spinocerebellar ataxia, subjects subjected to the trial are with genotypically confirmed spinocerebellar ataxia type 2 or spinocerebellar ataxia type 3. Subjects' baseline SARA score are in the range of 5 to 15.

$2.5 \times 10^7$ cell/kg bodyweight of Sternchymal® was thawed, prepared and loaded into syringe. Cells were injected slowly within one hour of thawing. Stemchymal® was intravenously infused to each subject and cell dosing was carried out three times at an interval of once every two weeks. After one or more treatment cycles, the SARA score of the subjects decreased and SCA2 or SCA3 condition improved.

What is claimed is:

1. A method for treating a polyglutamine (polyQ) disease comprising, parenterally or locally administering an effective amount of isolated adipose tissue derived mesenchymal stem cells (ADMSCs) that express cell markers CD273, CD46, CD55 and CXCR4 to a subject in need thereof, wherein the ADMSCs are administered in one or more treatment cycles, wherein each treatment cycle comprises the administration of the ADMSCs cells that express cell markers CD273, CD46, CD55 and CXCR4 as three separate unit dosages and the unit dose is administered at an interval of two to six weeks, and each unit dosage ranges from $0.5 \times 10^5$ to $5 \times 10^7$ cells/kg body weight of the subject.

2. The method of claim 1, wherein the polyQ disease is polyQ mediated spinocerebellar ataxias (SCA), Machado-Joseph disease (MJD/SCA3), Huntington's disease (HD), dentatorubral pallidoluysian atrophy (DRPLA) or spinal and bulbar muscular atrophy, X-linked 1 (SMAX1/SBMA).

3. The method of claim 2, wherein the SCA is SCA1, SCA2, SCA3, SCA6, SCAT or SCA17.

4. The method of claim 2, wherein the SCA is SCA2, SCA3 or SCA6.

5. The method of claim 2, wherein the SCA is SCA3.

6. The method of claim 1, wherein the parenteral administration is intramuscular, intravenous, intraarterial, or subcutaneous administration.

7. The method of claim 1, wherein the parenteral administration is intravenous administration.

8. The method of claim 1, wherein the local administration is intrabrain or intracranial administration.

9. The method of claim 1, wherein the local administration is intracranial administration.

10. The method of claim 1, wherein the unit dosage ranges from $0.5 \times 10^5$ to $5 \times 10^6$ cells/kg body weight.

11. The method of claim 1, wherein after the first treatment, the second treatment cycle is to be performed if the subject maintains total SARA score higher than 5 for one month.

12. The method of claim 1, wherein the unit dose is administered at an interval of two weeks.

13. The method of claim 1, wherein the ADMSCs can be co-administered with one or more additional therapeutic agents or in connection with another therapeutic intervention, either simultaneously or sequentially in any order.

* * * * *